(12) United States Patent
Braeken et al.

(10) Patent No.: US 8,569,006 B2
(45) Date of Patent: Oct. 29, 2013

(54) CELL-ENZYME BASED BIOSENSORS

(75) Inventors: Dries Braeken, Overpelt (BE); Danielle Rand, Leuven (BE); Carmen Bartic, Wilsele (BE)

(73) Assignees: IMEC, Leuven (BE); Katholieke Universiteit Leuven, K.U. Leuven R&D, Leuven (BE)

( * ) Notice: Subject to any disclaimer, the term of this patent is extended or adjusted under 35 U.S.C. 154(b) by 0 days.

(21) Appl. No.: 12/919,725

(22) PCT Filed: Feb. 29, 2008

(86) PCT No.: PCT/EP2008/001766
§ 371 (c)(1),
(2), (4) Date: Aug. 26, 2010

(87) PCT Pub. No.: WO2009/106101
PCT Pub. Date: Sep. 3, 2009

(65) Prior Publication Data
US 2011/0003322 A1    Jan. 6, 2011

(51) Int. Cl.
*C12Q 1/52* (2006.01)
(52) U.S. Cl.
USPC .......................................................... 435/16
(58) Field of Classification Search
None
See application file for complete search history.

(56) References Cited

U.S. PATENT DOCUMENTS

| 4,812,220 A | 3/1989 | Iida et al. |
| 6,225,047 B1 | 5/2001 | Hutchens et al. |
| 2003/0198967 A1 | 10/2003 | Matson et al. |
| 2007/0026382 A1 | 2/2007 | Lynes et al. |
| 2010/0248284 A1 | 9/2010 | Chen et al. |

FOREIGN PATENT DOCUMENTS

| WO | WO97/35616 A | 10/1997 |
| WO | WO01/43869 A | 6/2001 |
| WO | WO02/46756 A | 6/2002 |
| WO | WO03/042233 A | 5/2003 |
| WO | WO2007/084076 A | 7/2007 |

OTHER PUBLICATIONS

Braeken et al "L-Glutamate Detection Using a Poly-L-Lysine Coated EFNET", Proceedings of SPIE vol. 5839, SPIE, Bellingham WA, Edited by Ricardo A. Carmona and Gustavo Linan-Cembrano, (2005) p. 443-452.*
Yao et al. "L-Gluatamate enzyme electrode involving amplification by substrate recycling." (1990), Analytica Chimica Acta, vol. 236, pp. 437-440.*
Yang et al. "Dual-enzyme, co-immobilized capillary microreactor combined with substrate recycling for high-sensitive glutamate determination based on CE." (2009), Electrophoresis, vol. 30, pp. 3527-3533.*
Chaubey et al. (2001) Appl. Biochem. Biotechnol. 96, 239-248.
Castillo et al. (2005) Biosens. Bioelectron. 20, 1559-1565.
Jun et al. (2007) J. Neurosci. Methods 160, 317-326.

(Continued)

*Primary Examiner* — Ralph Gitomer
*Assistant Examiner* — Teresa E Knight
(74) *Attorney, Agent, or Firm* — Knobbe Martens Olson & Bear LLP (57) ABSTRACT

The invention relates to a sensor comprising a sensing layer and a surface layer, wherein said surface layer comprises, a first region suitable for adherent growth of cells, and a second region, adjacent to said second layer, suitable for the attachment of proteins, wherein the first and second region are in contact with the sensing layer.

26 Claims, 5 Drawing Sheets

(56) References Cited

OTHER PUBLICATIONS

Bernard et al. (1998) Langmuir 14, 2225-2229.
Barbulovic-Nad et al. (2006) Critic. Rev. Biotechnol. 26, 237-259.
Annex to Official Communication in equivalent EP Appl. No. 08716283.0 dated Mar. 12, 2012.
Braeken, D. "L-glutamate detection using a poly-L-lysine coated ENFET", Proceedings of SPIE, vol. 5839, Jan. 1, 2005, pp. 443-452.
Lehmann et al., "Simultaneous measurement of cellular respiration and acidifications with a single CMOS ISFET" Biosensors and Bioelectronics, Elsevier BV, NL LNKD-DOI:10.1016/S0956-5663(01)00123-3, vol. 16, No. 3, May 1, 2001, pp. 195-203.
Parton et al., "Patterning Neurons-On-Chip Devices Using Microcontact Printing", Solid State Technology, Pennwell Corporation, Tulsa, OK, US, vol. 48, No. 12, Dec. 1, 2005, p. 28, 30.
Rand et al., "Surface Amplification of L-Glutamate Using a Patterned Bienzymatic System for Biosensing Applications" IEEE Transactions on Nanotechnology, vol. 10, No. 1, Jan. 2011, pp. 102-110.
Schoning et al., "Bio FEDs (Field-Effect Devices): State-of-the-Art and New Directions" Electroanalysis, vol. 18, No. 19-20, 2006, pp. 1893-1900.
Valero et al., "A Continuous Spectrophotometric Method Based on Enzymatic Cycling for Determining L-Glutamate", Analytical Biochemistry, vol. 259, Jan. 1, 1998, pp. 265-271.

\* cited by examiner

GLOD
GPT

Figure 8

CELL-ENZYME BASED BIOSENSORS

CROSS-REFERENCE TO RELATED APPLICATIONS

This application is the national phase under 35 U.S.C. §371 of prior PCT International Application No. PCT/EP08/001,766 which has an International Filing Date of Feb. 29, 2008, which designates the United States of America, the disclosure of which is hereby expressly incorporated by reference in its entirety and is hereby expressly made a portion of this application.

FIELD OF THE INVENTION

The present invention relates to the field of sensors and/or surface chemistry and more particularly to the chemical modification of micro-electronic on-chip sensors for the detection of neurotransmitters.

BACKGROUND OF THE INVENTION AND STATE OF THE ART

Neurons communicate with each other in a neuronal network by firing action potentials. These electrical signals are converted into a chemical signal in the synapses between the neurons. Molecules responsible for this action are called neurotransmitters. The neurotransmitter L-glutamate is one of the most important chemical messengers in the synapses of the central nervous system. Detection of glutamate allows to monitor neuronal activity, which is a desirable tool e.g. for neurological research into neurodegenerative diseases, screening systems for neurotoxic compounds, screening of drugs that can influence synaptogenesis or synaptic activity. The detection of glutamate, a taste enhancer, also has applications in food industry.

Selective detection of glutamate can be done using glutamate agonists (e.g. AMPA (alpha-amino-3-hydroxy-5-methyl-4-isoxazole propionic acid)) or by enzymatic detection. The current on-chip enzymatic detection techniques rely on microelectrodes or ion-selective field-effect transistors (ISFET). Microelectrodes monitor the redox current upon catalysis of glutamate by the enzyme, while ion-sensitive field-effect transistors measure any change in local pH or charge at its liquid/surface interface.

Monitoring the chemical activity of neurons, requires a fast response, i.e. a sensor that quickly generates a detectable signal, in order to be able to monitor the activity in real time in the same time scale as the signal of the neurons. This speed relies not only on the rate of the chemical reaction that is selective for glutamate, but also on the swiftness of the sensor to pick up a detectable product of such chemical reaction and create a recognisable signal. Furthermore, due to the minute amount of neurotransmitters that is released by a neuron into the synaptic cleft, and the rapid diffusion of these molecules, a highly sensitive sensor is needed. For such purposes, field-effect transistors constitute prime candidates due to their fast response and their inherent, amplifying nature, and their ease to be miniaturised and integrated into large arrays with read-out/drive electronics.

Different enzymes exist that selectively catalyse glutamate and generate a detectable (side) product.

Glutamate Dehydrogenase catalyses the reaction between L-glutamate, water and $NAD^+$ to form 2-oxoglutarate and NADH. The side products of this reaction are ammonia and protons, and as such cause a change in pH. The enzyme, however, relies on exogenously added $NAD^+$.

Glutamate Decarboxylase breaks down L-glutamate into 4-aminobutanoate and $CO_2$. In water, $CO_2$ generates carbonic acid, resulting in a decrease in pH. Glutamine Synthetase requires ATP and ammonium to convert L-glutamate into L-glutamine, and generates ADP and phosphate as side products. This approach has previously been reported (U.S. Pat. No. 4,812,220). The addition of exogenous ammonium as a substrate for the enzymatic reaction can be harmful for a neuron culture.

Glutamate Oxidase (GLOD) consumes only water and oxygen to convert L-glutamate into 2-oxoglutarate. The side products are ammonia and hydrogen peroxide, which cause a local change in pH.

In order to create a highly sensitive glutamate sensor, and as such accelerate its response, a lower limit of detection can be achieved by chemically amplifying the L-glutamate concentration, using a so-called "bienzymatic system" wherein the product of a first enzyme is the substrate of a second enzyme and vice versa. This chemical amplification principle has previously been demonstrated for the detection of lactate (Chaubey et al. (2001) *Appl. Biochem. Biotechnol.* 96, 239-248).

Figure 2:
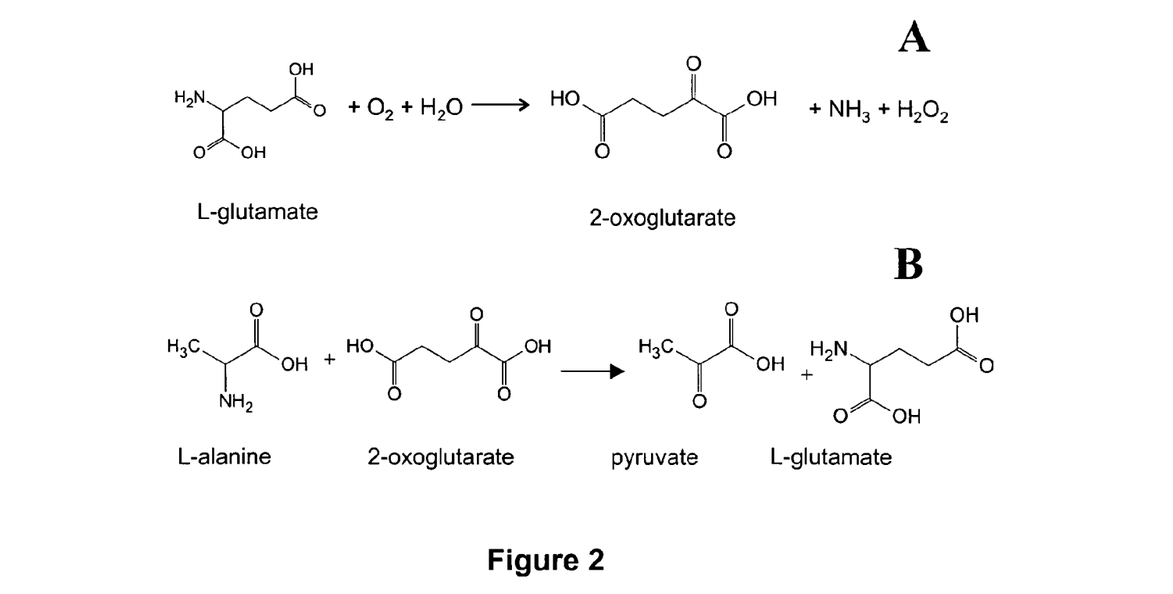
FIG. 2 shows the enzymatic conversion of glutamate by Glutamate Oxidase (GLOD) (A) and the conversion of oxoglutarate by L-Glutamate-Pyruvate Transaminase (GPT) (B).
Figure 3:
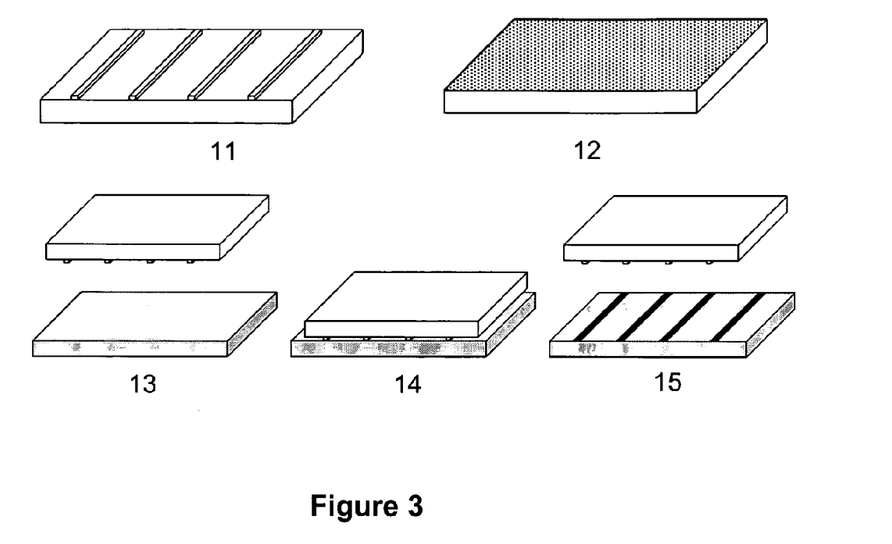
FIG. 3 shows a schematic overview of microcontact printing according to an embodiment of the invention. A polydimethylsiloxane (PDMS) stamp (11) is inked with the target molecule (12). The stamp is then brought into contact with the substrate (13 and 14) and prints the target molecule onto the substrate in the pattern (15) determined by the stamp.

L-Glutamate Pyruvate Transaminase (GPT), can complement Glutamate Oxidase or Glutamate Dehydrogenase to form a bienzyme pair that amplifies the amount of L-glutamate produced by a cell. Glutamate Pyruvate Transaminase recycles 2-oxoglutarate from the first enzymatic reaction (with Glutamate Oxidase or Glutamate Dehydrogenase) and converts it back into L-glutamate (FIG. 2). The amino acid L-alanine is required to start and fuel this recycling reaction. Pyruvate is a side product of the reaction. As long as alanine is provided, a single molecule of L-glutamate cycles through this closed enzymatic loop and continues to generate ammonia and hydrogen peroxide as detectable products.

This bienzyme system is commercially available for the detection of Glutamate Oxidase in a solution [Molecular Probes, Invitrogen, the Netherlands]. Herein, the generation of $H_2O_2$ is used in a colorimetric reaction. Parton et al. (2005) in *Solid State Technol.* describe a glutamate sensor wherein a field effect transistor is covered with a layer of Glutamate Oxidase. This layer forms the contact between the electronic device and the neurons which adhere on top of this layer.

Castillo et al. (2005) *Biosens. Bioelectron* 20, 1559-1565, describe a sensor for the detection of glutamate wherein cells, growing on a porous membrane, are placed above an electrode comprising a hydrogel with Glutamate Oxidase. These authors emphasise that is it important to avoid contact of the cells with the electrode surface.

AIMS OF THE INVENTION

The aim of the invention is to provide improved enzyme based sensors, which have a lower limit of detection, a higher sensitivity than a single enzyme functionalised FET, have a faster response and are non-toxic for cell cultures, in particular neuronal cultures.

SUMMARY OF THE INVENTION

Figure 1:
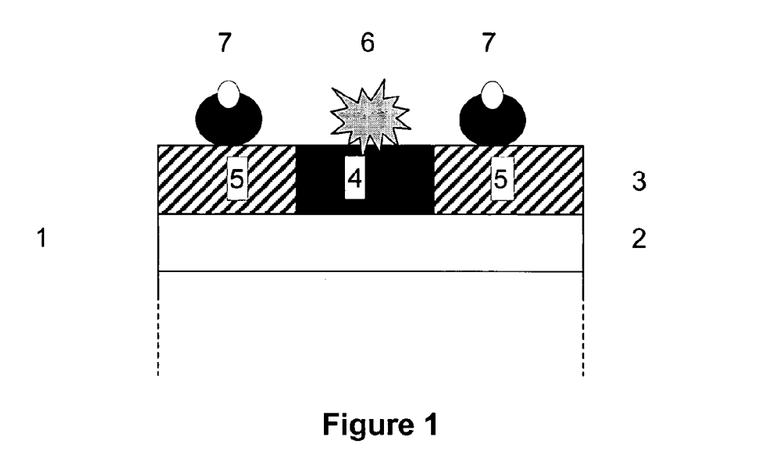
FIG. 1 shows a schematic overview of an embodiment of a sensor (1) according to the present invention (2: sensing layer; 3: surface layer; 4: first region; 5: second region; 6: cells; 7: enzyme)

In one aspect of the invention sensors are provided comprising a region for growing cells and a region for enzymatic conversion, which are situated such that sensitive detection is ensured. In particular embodiments, the sensors (1) comprise a sensing layer (2) and a surface layer (3), wherein the surface layer comprises a first region (4) suitable for adherent growth of cells (6), and a second region (5), suitable for the attachment of proteins, wherein the first and second region are in contact with the sensing layer. In particular embodiments, the first region (5) and the second region (5) are physically separated but adjacent to each other. In further particular embodiments the second region (5) comprises at least one enzyme for the conversion of a compound produced by the cells into a product which generates a detectable signal. Accordingly, particular embodiments of this aspect of the invention are devices which comprise a sensor (1) comprising a sensing layer (2) and a surface layer (3), wherein the surface layer comprises a first region (4) suitable for adherent growth of cells (6), and a second region (5), adjacent to the first region, to comprising at least one enzyme (7) for the conversion of a compound produced by the cells into a product which generates a detectable signal, wherein the first and second region are in contact with the sensing layer. The surface layer of the sensor thus comprises two regions.

In particular embodiments of sensors described herein, the first region comprises cells, such as neuronal cells.

In particular embodiments of sensors described herein, the first region and/or the second region consist of a plurality of linear elements. More particularly, sensors are provided wherein the linear elements of the first region have a width of about between 5 and 20 micrometer. Additionally or alternatively, sensors described herein have a second region with linear elements which have a width of between 2 and 20 micrometer.

In further particular embodiments of sensors described herein, the first region and/or the second region consist of a grid like pattern of a plurality of linear elements.

According to particular embodiments of the invention sensors are provided comprising at least one enzyme whereby the at least one enzyme is a bienzyme system, such as, but not limited to a bienzyme system comprising Glutamate Oxidase or Glutamate Dehydrogenase and L-Glutamate Pyruvate Transaminase.

According to the invention sensors are provided wherein the second region is envisaged to be suitable for the attachment of proteins. More particularly, sensors are provided wherein the second region comprises at least one enzyme which generates a detectable signal by conversion of a compound produced by cells present in the first region. In further particular embodiments the compound produced by the cells is a neurotransmitter, such as glutamate.

A further aspect of the invention relates to methods for the detection of cellular responses, more particularly based on the detection of a compound produced by the cells. Accordingly methods are provided for the detection of the production of a compound by a cell. In particular embodiments, the methods comprise detecting a signal generated by enzymatic conversion of a compound produced by a cell. In particular embodiments, sensors such as those described herein are used. Accordingly, in particular embodiments methods are provided which comprise the steps of providing cells in a first region of a sensor, providing at least one enzyme capable of converting a compound produced by the cells into a product whereby a detectable signal is generated in a second region of the sensor and ensuring conditions for the conversion of the compound into a product which generates a detectable signal, whereby the first and the second region of the sensor are located such that the product generated by the cells in the first region can be converted by the at least one enzyme in the second region and whereby the second region is located such that the sensor can detect the detectable signal. More particularly, the first and the second region are located adjacent to each other and are in contact with the sensing layer of the sensor.

Accordingly, particular embodiments of the invention relate to methods for detection of cellular responses which comprise the steps of providing a sensor as described above comprising at least one enzyme capable of converting a compound produced by the cells into a product which generates a detectable signal, providing appropriate cells in the first region of the sensor, providing conditions for the conversion of a compound produced by the cells into a product which generates a detectable signal, and detecting the detectable signal.

According to particular embodiments of methods described herein, the detectable signal is a change in pH.

Yet a further aspect of the invention relates to methods for producing a sensor, more particularly methods for producing a surface layer on a sensor. More particularly the surface layer comprises a first and a second region, which are provided on the sensor as physically separated but adjacent to each other. In particular embodiments, methods are provided which comprise the steps of providing a sensor surface with a sensing layer (2), applying a first region (4) of a surface layer on/within the sensing layer, wherein the first region is suitable for adherent cell growth, and applying a second region (5) of a surface layer on/within the sensing layer, wherein the second region is suitable for the attachment of proteins, whereby the first and second region are in contact with the sensing layer. The first and second region can be provided either simultaneously or sequentially, the order being immaterial to the invention.

According to particular embodiments of methods according to this aspect of the invention described herein, at least one of the first and second region are applied by contact printing.

Particular embodiments of methods described herein comprise a separate step of applying at least one enzyme to the second region. In alternative embodiments, the enzyme is applied upon application of the second region. According to particular embodiments of methods described herein the enzyme is applied by contact printing.

Particular embodiments of methods according to this aspect of the invention described herein comprise the step of applying cells to the first surface layer in the first region.

Another aspect of the invention relates to the use of a sensor with a sensing layer and a surface layer in contact with the sensing layer comprising immobilised cells in a first region of the surface layer, and an immobilised enzyme in a second region of the surface layer, for the detection of a product obtained by the enzymatic conversion by the enzyme of a compound produced by the cells.

Particular embodiments of uses described herein comprise the use wherein the cells are neuronal cells and the compound is a neurotransmitter.

DETAILED DESCRIPTION OF THE INVENTION

Definitions

The term "region" as used herein referring to a layer, refers to a part of that layer. A region can be continuous or be built up from a plurality of sub-parts (e.g. lines). Such sub-part is referred to as an "element".

"Cell attachment region" refers to a region, which is functionalised for the attachment of cells. Where a surface layer comprises different regions, this region is also referred to as the "first region".

"Immobilisation region" refers to a region, which is functionalised for the attachment of proteins and cells. Where a surface layer comprises different regions, this region is also referred to as the "second region".

A "bienzyme system" relates to a pair of different enzymes, whereby one enzyme converts a substrate (A) into a product (B) and the other enzyme uses this product (B) as its substrate converting it back into original substrate (A).

A first aspect of the present invention relates to enzyme-based sensors wherein a compound produced by a cell is converted by an enzyme into a product which generates a detectable signal. Compared to the direct detection of the compound, this conversion into a product which generates a detectable signal lowers the limit of detection of a sensor, renders it more sensitive and allows it to generate a measurable response more quickly.

The enzyme envisaged for use in the sensors of the invention can be any enzyme which converts a compound into a product which generates a detectable signal. The detection of the conversion product can be based on a change in local pH, a change in charge, an electron transfer, a colorimetric reaction, etc.

In particular embodiments, the enzyme is an enzyme which converts a neurotransmitter into a product whereby the conversion results in a local pH change. Examples include, but are not limited to enzymes which convert catecholamine, such as adrenaline, noradrenaline and dopamine (Tyrosinase), glucose (glucose dehydrogenase, glucose oxidase), acetylcholine (acetylcholine esterase), and glutamate (Glutamate Dehydrogenase, Glutamate Decarboxylase, Glutamine Synthetase, Glutamate Oxidase).

In particular embodiments the sensor is based on one enzyme. In more particular embodiments two enzymes of a bienzyme pair are used to convert a compound and generate a detectable signal. This allows an amplification of the signal.

Examples of bienzyme systems include but are not limited to lactate dehydrogenase and lactate oxidase for the detection of lactate.

In particular embodiments of methods and sensors of the present invention the bienzyme system consists of Glutamate Dehydrogenase/Glutamate Pyruvate Transaminase or of Glutamate Oxidase/Glutamate Pyruvate Transaminase.

Different types of sensors are suitable for the methods and devices of the present invention such as field-effect transistors (FET), ion-selective field-effect transistors (ISFET), capacitive sensors or microelectrodes. The sensor comprises a sensing layer and detects a signal generated at or near the surface of the sensing layer. The signal can subsequently e.g. modify the conductivity in the channel region in a FET. Ion-sensitive Field-Effect Transistors (ISFET) have a pH sensitive gate layer acting as sensing layer. Any change in charge distribution (a change in pH, a change of charged moieties, . . . ) adsorbed at or created near the gate of the FET will modulate the conductivity of the channel underneath.

Micro-electrodes can either measure the redox currents involved in the catalysis of glutamate by the enzymatic system, or can act as a pH electrodes when functionalised with a pH-sensitive layer. As a pH electrode, a micro-electrode combined with a reference electrode, measures any change in voltage difference across the pH sensitive layer that arises from changes in pH or from different charging of the double layer capacitance.

The relevant parts of a sensor in accordance with an embodiment of the present invention include a sensing layer (2) and a surface layer (3), whereby the surface layer (3) comprises a first region (4), which is the cell attachment region and a second region (5), which is the immobilisation region for enzymes. The sensors of the invention are characterised in that the first and second region are physically separated but adjacent to each other and both in direct contact with the sensing layer.

A further particular embodiment of a sensor according to the invention is depicted in FIG. 1. The sensor (1) comprises a sensing layer (2). Cells (6) are located on a first region (4) (cell attachment region). One or more enzymes (7) are located on a second region (5) (immobilisation region). The sensing layer (2) is in contact with remaining parts of the sensor for transferring a detected signal.

The sensing layer (2) of the sensors in accordance with the present invention is water-insoluble, and comprises for example an inorganic oxide layer such as $SiO_2$ or $Ta_2O_5$. A sensing layer alternatively comprises a noble metallic layer such as Au or Pt. Alternatively, a sensing layer comprises an oxidisable metallic layer such as Ta or Ti or an oxidisable semiconductor layer such as Si. The sensing layer alternatively comprises a III-V layer such as GaAs or GaN.

The sensing layer (2) of sensors described herein is an integral functional part of the sensor such that a signal generated at/near its surface or in its bulk can be detected by the sensor.

Non-restrictive examples of pH sensitive (gate) layers are described below, whereby any of these layers can function as a sensing layer. An oxide is intrinsically pH sensitive since it can bind $OH^-/H^+$ at its surface. A metal layer can be rendered (more) pH sensitive by adsorbing an organic layer comprising pH sensitive functional groups such as amino, carboxylic acid and (hydro)quinone. A metal layer can also be covered with an intentionally deposited oxide or with its native metallic oxide, which are both intrinsically pH sensitive. A semiconductor layer can act in itself as a pH sensitive layer but can also be covered with a pH sensitive layer such as an oxide or a metal with an adsorbed layer as described before, or with said organic pH sensitive layer adsorbed directly on the semiconductor. An oxide can be functionalised with a layer containing pH sensitive groups (e.g. amino, carboxyl, hydroquinone) in order to improve its mV/pH response.

According to the invention, sensors are provided which comprise one or more immobilisation regions. An immobilisation region is a region of the surface of the sensor suitable for immobilising one or more enzymes such as a bienzyme system. In particular embodiments the immobilisation region comprises the one or more enzymes. As detailed below, different materials are envisaged to be suitable for use in an immobilisation region. Some of these materials are also suitable for use in one or more other parts of the sensor e.g. the sensor layer and/or the cell attachment region of the sensor surface. Accordingly, immobilisation region(s) is/are either one or more dedicated region(s) within the sensor material or is provided on the sensor layer as a surface layer or as part(s) of a surface layer. In either embodiments, the immobilisation region(s) can be a continuous region or provided as one or more two or three-dimensional structures which is/are in any case if not part of directly in contact with the sensor surface.

Where the immobilisation region is provided as a separate layer or part thereof, the thickness of the layer preferably is below 1 micrometer. Preferably, the thickness is below 0.5 micrometer. This results in a sensor with a higher response time.

Examples of immobilisation regions provided as a layer comprise, but are not limited to self-assembling monolayers or mixed self-assembling monolayers. For example, a Self-Assembled Monolayer (SAM) of 16-mercaptohexadecanoic acid consists of 100% carboxyl groups. Mixtures comprising a polyethylene glycol (PEG) ended thiol, create a mixed carboxyl/PEG SAM.

Particular embodiments of an immobilisation region relate to a layer of one or more molecules which comprise functional groups which ensure adherence to the sensor surface and functional groups which bind one or more functional groups on the one or more enzymes. Chemical functions suitable for immobilising an enzyme in the immobilisation region include functional groups that are intrinsically reactive and groups that require activation to become reactive. Non-restrictive examples of "immobilisation functions" that can bind with innate reactive functions on enzymes are aldehydes, acrylates, carboxylic acids, amino groups and thiols.

In particular embodiments one or more enzyme(s) are bound to the immobilization region by a functional group or are derivatised with at least one active moiety, such as an aldehyde Accordingly, the immobilisation of enzymes onto the immobilisation region or second region can be done in different ways including covalently, by adsorption, by crosslinking, by entrapment, or by a combination of the aforementioned methods. Non-restrictive examples of these immobilisation methods are described in U.S. Pat. No. 4,812,220, which is incorporated by reference. Examples hereof are covalent immobilisation via bonding to an amino group, absorption via immobilisation with an ion bond or a physical force, crosslinking with compounds such as glutaraldehyde, and entrapment immobilization with chemical reactions with monomers, crosslinker, and initiator.

As indicated above, in particular embodiments the immobilisation region is a layer comprising organic molecules such as self-assembling monolayers or mixed self-assembling monolayers with appropriate chemical functions which ensure that the immobilisation layer links to the sensing layer and chemical functions which ensure that the one or more enzymes specifically bind in the immobilisation region. The linking of molecules to the sensor surface can be covalent, ionic, . . . etc. Non-restrictive examples of linking functions are silanes on oxide surfaces (e.g. $SiO_2$, $TiO_2$, $Ta_2O_5$), thiols on metals (e.g. Au, Pt) or III-V materials (e.g. GaAs), carboxylic acids and phosphonates ($PO_3^-$) on metal oxides and on III-V materials, sulfonates ($SO_3^-$) on III-V materials, and amino on gold.

The immobilisation region can comprise subsequently applied multiple layers with or without chemically reactive interlayer. An immobilisation layer can also be a gel or a polymer comprising similar chemical functional groups for adhering and binding. An immobilisation layer can comprise chemical functions that tune and/or improve the sensitivity of the sensor. An immobilisation layer can comprise chemical functions (e.g. poly-ethylene glycol) that reduce non-specific adsorption of non-targets and/or improve/maintain the conformation of the bound bienzyme pair.

Increasing the number of immobilisation sites for enzymes (the creation of 3D surfaces) an immobilisation region can be obtained by attaching dextran chains to the surface. Enzymes can couple to the carboxyl groups of the dextran chains by e.g. EDC/NHS.

In particular embodiments enzymes are immobilised in the immobilisation region by way of polymers, which can be either attached directly to the sensor surface or which can be attached to a self assembled monolayer such as those mentioned above. A polymer is a more complex structure and is not considered a monolayer. As such a polymer thickens the immobilisation layer but it has the main advantage of largely increasing the number of binding sites for enzymes to couple on.

In particular embodiments, the immobilisation region comprises more than one enzyme. When more than one enzyme is immobilised, such as enzymes of a bienzyme pair, particular immobilisation techniques for obtaining the sensors according to the invention may be required. Thus, two or more enzymes are immobilised either in a consecutive way or simultaneously from e.g. a mixed solution, depending on whether their optimal deposition/immobilisation conditions are conflicting. These deposition conditions can be influenced by the nature of the immobilising chemical functions and their activation scheme. In particular embodiments the enzyme which produces the product which generates a detectable signal is spotted at dedicated places to locally concentrate the enzyme and consequently the detectable product.

Enzymes of bienzyme pairs are immobilised generally in a ratio within the range of e.g. 100/1, 50/1, 20/1, 10/1, 5/1 and 1/5, 1/10, 1/20, 1/50 and 1/100. In particular embodiments of the sensors and methods of the present invention, the immobilisation region comprises a bienzyme pair of GLOD and GTP. Such sensors can be used, inter alia, for determining the presence of L-glutamate in a qualitative way, or to quantitatively determine the amount of L-glutamate. In the latter case, alanine can be used to titrate the concentration of glutamate. The determination of quantitative measurements depends on the concentration of glutamate, of the concentration of alanine, of the ratio of the concentration of the two types of enzymes immobilised on the surface, and of the reaction rate of both enzymes and any variable that influences this reaction rate.

The sensors according to the present invention further comprise one or more cell-adhering regions, i.e. a region suitable for adhering cells. Again, as for the immobilisation region, a cell-adhering region can be one or more dedicated areas on the sensor surface or can be one or more two- or three-dimensional structures located on and in close contact with the sensor surface. The cell-adhering region(s) is/are comprised within the surface layer together with the immobilisation region(s).

In particular embodiments, the one or more cell-adhering regions comprise organic adhering chemical functions. The nature of an organic adhering chemical function suitable in the context of the invention is determined by the nature of the surface and the cells envisaged to adhere. Typical molecules which are suitable for ensuring cell adherence are molecules naturally involved in cell adherence including cell adhesion molecules (CAM) including a) immunoglobulin superfamily CAMS (IgSF CAMs) including Neural Cell I Adhesion Molecules (NCAMS), Intercellular Cell adhesion Moleculs (ICAM), Vascular Cell Adhesion Molecule (VCAM), Platelet endothelial Cell adhesion Molecule (PECAM), etc., b) Integrins, c) selectins and d) cadherins. However, the use of small molecule-type adhering compounds is also envisaged.

In particular embodiments the material of the sensing layer is suitable for use in an immobilisation region and/or a cell-adhering region. This is the case, for instance, when the sensing layer contains pH-sensitive groups which can also adsorb proteins. An example hereof is Poly-L-Lysine (PLL), which contains an abundant amount of amino groups. Poly-L-lysine can be covalently attached to a metal surface via its amino groups to the activated carboxyl groups of a thiol-self assembling layer. Poly-L-lysine can also be bound via its positively charged amino groups onto a negatively charged surface such as gold. Enzymes are optionally coupled to the PLL backbone via a cross linker such as glutaraldehyde. In such embodiments, the immobilisation region and/or cell-adhering region of the surface layer can be provided as dedicated regions of the sensing surface.

The sensors and methods of the invention are in principle applicable for any type of cell. The suitability of the sensor is determined by the availability of an enzyme system which interacts with a compound which is relevant for detection. Accordingly, sensors according to the invention allow the monitoring of processes which involve the production of compounds which can be the detected by an enzymatic conversion into a detectable signal. Cells can be bacterial cells, fungal cells, plant cells, or animal cells.

In particular embodiments, the cells are neuronal cells or neuron-like cells such as cultured cell lines secreting neurotransmitters. Such cells may be human cells but may also be obtained from any other model organism such as rats, non-human primates, or more primitive model organisms such as *Aplysia*.

The position of the cells is arranged such that the distance between the cell and sensor surface is as small as possible. This distance differs from cell to cell but is for mammalian neuronal cells typically below 50 nm, below 20 nm, below 10 nm, or even below 5 nm, allowing a high sensitivity which is needed to detect sometimes minute amounts of a compound produced by a cell such as neurotransmitter released in the synapse. This can be achieved by guiding and confining the growth of the neuronal cell growth on top of the sensor, more particularly within the cell-adhering region.

The sensors according to the invention comprise one or more cell-adhering (first) region(s) and one or more immobilisation (second) region(s) which are located on the sensor surface such that an enzyme on the second region is in proximity with the cells on the first region. Depending on the type of cells and the type of material used for the first and second regions, cells may grow exclusively in the first region. Optionally, physical or chemical barriers are provided to avoid growth of the cells outside the first region.

In particular embodiments of the invention such as illustrated by the examples herein, the cells do not grow on the enzyme layer because they cannot adhere. In these embodiments of the invention, the enzyme is deposited in specified patterns (making up the immobilisation region) on the sensor layer before the cells are seeded on the surface, leaving a favourable surface for cell adhesion. For example, as described above, the surface layer of poly-L-lysine (PLL) is a suitable surface for both cell and enzyme adhesion. Accordingly, the enzyme layer is patterned such that adequate regions of PLL remain after deposition.

In particular embodiments, the sensor comprises on its sensor surface a pattern of regions, wherein an enzyme is immobilised in the second region(s), and cells adhere to the first region(s). This pattern is a particular embodiment of a surface layer on the sensor surface. A surface layer wherein cells and enzyme(s) are at an optimal distance from each other can be obtained in different ways. For instance, this can be obtained by a surface layer, wherein the cell-adhering regions occur as linear lines, circular lines, or grids whereby the remainder of the surface layer represent immobilisation regions. Alternatively, immobilisation region(s) occur as linear lines, circular lines, or grids, with the remainder of the surface layer cell-adhering region. Further embodiments include surface layers comprised of alternating lines, grids or circles of immobilisation and cell-adhering regions. Various other arrangements can be designed wherein cell-adhering (first) regions and enzyme immobilising (second) regions are arranged with respect to each other.

Figure 7:
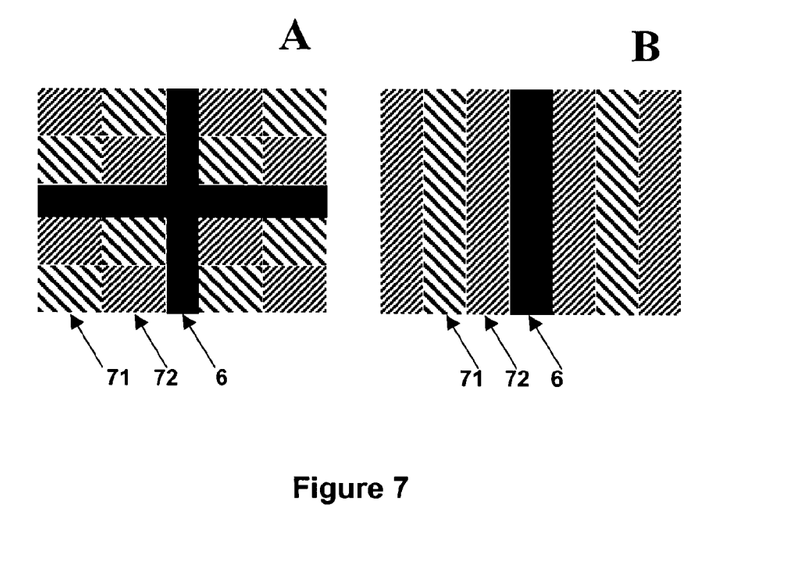
FIG. 7 shows examples of sensor surfaces in accordance with embodiments of the invention. 6 are first region elements with cells; 71 and 72 are elements of the second region for the attachment of respectively a first enzyme and a second enzyme of a bienzyme system.
Figure 8:
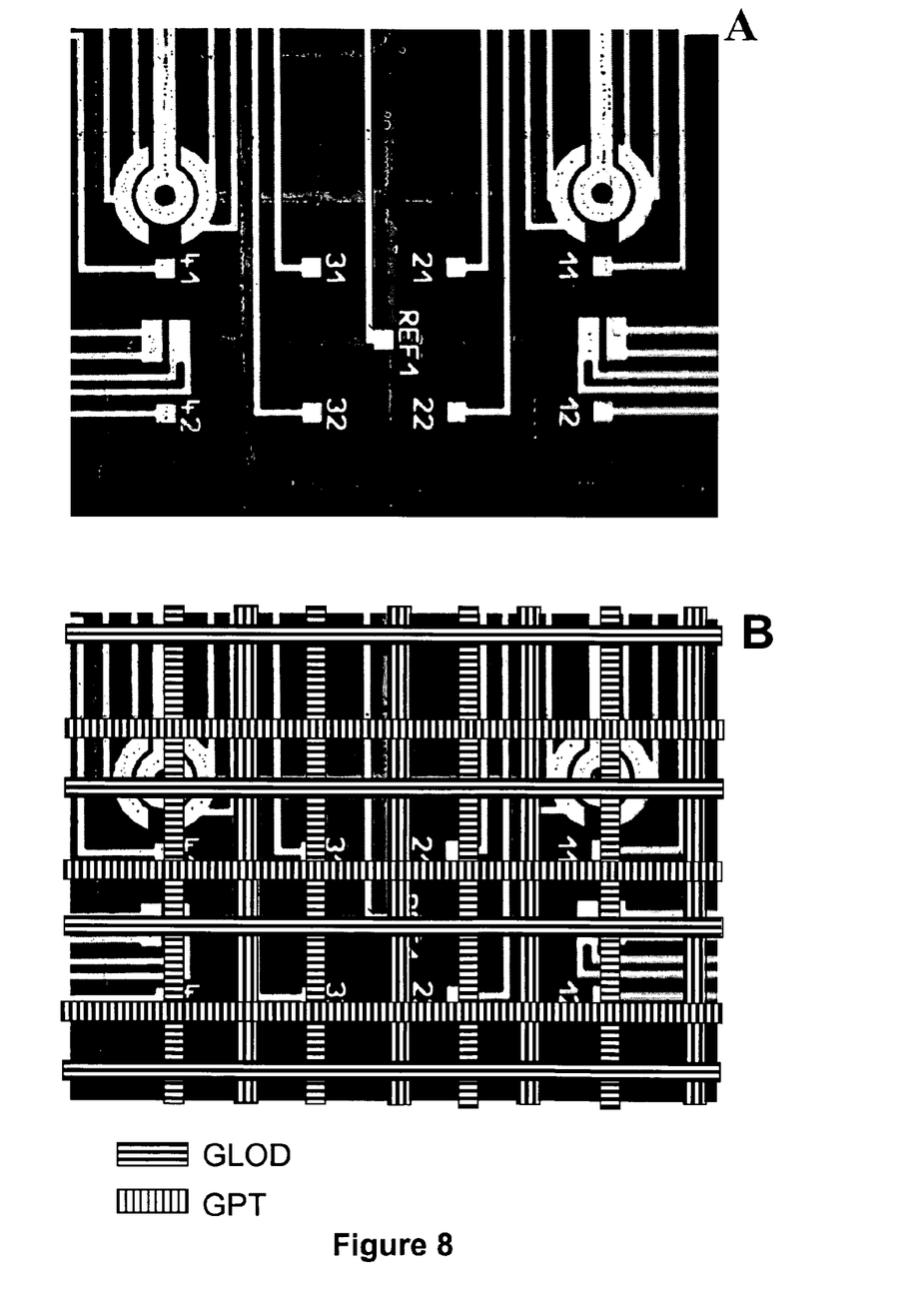
FIG. 8 shows sensors prepared by microcontact printing. Panel A shows a photograph of a sensor surface with grids of GLOD and GPT (4 μm width) which were aligned by microcontact printing on the surface of a chip in a 50-μm shift both horizontally and vertically.
Panel B shows the same photograph where the lines of GLOD are represented with bars with longitudinal lines and the lines of GPT with bars with traverse lines.

In such patterned arrangements, the first and/or second region of a sensor is in fact comprised in different parts, which are also referred to as "elements" throughout this application. Non-limiting arrangements of first regions and second regions are shown in FIGS. 7 and 8. Typically, the entire surface of the sensor is used covered by the cell-adhering and immobilisation regions for the application of cells and enzyme. However, other embodiments are envisaged wherein e.g. different spots of cells are surrounded by a (circular) zone of enzyme, or vice versa, creating an array of different sensor elements whereby the resulting surface layer is also discontinuous.

Generally, the smallest dimension of an element of a first region is in the range of 5 to 20 µm, depending on the cell type. Generally, the smallest dimension of an element of a second region is in the range of 2 to 20 µm.

Particular embodiments of the present invention include sensors wherein proteins (enzymes) occur in the immobilisation regions as e.g. linear or circular elements. Such sensors nevertheless show a clear difference from prior art protein micro arrays, such as arrays of adhesion molecules for screening cell binding. In the prior art arrays, the surface of the array is treated to avoid aspecific binding of interfering compounds (aspecific cell or protein binding). Sensors according to the present invention envisage the binding of cells in the cell-adhering region(s) adjacent to the immobilisation region.

Particular embodiments of the present invention provide sensors comprising a sensor surface of a material which is equally suitable for use in the cell-adhering region and/or the immobilisation region. For instance, where the sensor surface is made of a pH responsive material which is suitable for cell adherence. On such sensors, as used in the present invention the enzymes and cells are localised on different dedicated regions of the sensor surface.

A further aspect of the invention relates to the generation of the sensors according to the invention. The surface layer comprising the first and the second regions can be applied by different methods. In particular embodiments, microcontact printing (comprising pin printing and microstamping) is used to pattern molecules onto a surface. The method involves fabricating a stamp by casting and curing an elastomeric polymer, such as polydimethylsiloxane, (PDMS), against a patterned master. This stamp is then inked with the target molecule that is desired to be printed on the substrate surface. Because the stamp is deformable, it makes conformal contact with the substrate, transferring the material on the relief structures of the stamp onto the substrate surface. This method has been used to spatially pattern neurons with poly-L-lysine (June et al. (2007) *J. Neurosci. Methods* 160, 317-326) and has also been exploited for the controlled patterning of a monolayer of various proteins and enzymes (Bernard et al. (1998) *Langmuir* 14, 2225-2229). Other techniques for applying proteins in spots or patterns, such as photochemistry-based methods, laser writing, electrospray deposition and inkjet technologies which are suitable are reviewed for example in Barbulovic-Nad et al. (2006) *Critic. Rev. Biotechnol.* 26, 237-259.

Aligned stamping is done through use of a flip chip bonder. A flip chip bonder is an instrument used to align and bond chips onto a substrate using heat and/or pressure. The complete operation consists of loading, alignment, bonding, and unloading. In normal operation, one of the two devices to be bonded is secured on a lower chuck, and the other is secured by an arm that "flips" it over 180° and then bonds with the lower substrate. Alignment is done visually by the user. This instrument is suitable to align and stamp the sensor substrate with enzyme.

Another aspect of the invention relates to methods for detecting a compound produced by a cell using sensors as described above. In this method a compound which is produced and released by a cell, adhering in a first region of a surface layer of a sensor, is converted by an enzyme, immobilised in a second region of the surface layer of the sensor, into a product which conversion yields a detectable signal. This detectable signal is sensed by the sensing layer of the sensor. In these methods all elements, namely cells, produced compound, enzyme, detectable signal and sensing surface are at a minimal distance from each other which enhances speed and sensitivity of detection.

In particular embodiments of methods of the invention, two enzymes forming a bienzyme pair are used to amplify the detectable signal generated by the conversion of the compound. In such methods, the enzyme which produces the detectable signal is present in the second region, while the other enzyme, which converts the product of the first enzyme back into the compound, is present either in solution, or is also present (e.g. immobilised) in the second region. In the latter case, both enzymes are either applied in the same elements of the second region or alternatively, the enzymes are applied in different elements of the second region, as shown for example in FIGS. 7 and 8.

In particular embodiments of the sensors and methods according to the invention, glutamate production by the cells is monitored. More particularly, glutamate production is monitored based on the enzymatic conversion of glutamate into ammonia and hydrogen peroxide, which cause a pH change. More particularly, glutamate detection relies on the generation of ammonia and hydrogen peroxide by Glutamate Oxidase.

In further particular embodiments, glutamate production is monitored with a bienzyme system, most particularly using Glutamate Oxidase (GLOD) and Glutamate Pyruvate Transaminase (GPT). The GPT enzyme recycles oxoglutarate into glutamate and as such does not produce a product which generates a detectable signal. The presence of a second enzyme making up an enzyme pair, such as GPT, on the second region is not obligatory, but increases the sensitivity and speed of the sensor.

EXAMPLES

Example 1

Preparation of a Surface Layer

In this embodiment, Glutamate Oxidase (GLOD) and Glutamate Pyruvate Transaminase (GPT) are immobilised on a metal surface of the floating gate of an ion sensitive field-effect transistor.

A Self-Assembled Monolayer (SAM) of 16-mercaptohexadecanoic acid is deposited from an ethanol solution on a metal surface of the floating gate of an ion sensitive field-effect transistor. The surface coverage can be 100% carboxyl groups or can be diluted with a polyethylene glycol (PEG) ended thiol to create a mixed carboxyl/PEG SAM. The mixed SAM was made using 5% PEG and 95% carboxyl. Upon activation of the carboxyl groups with 1-ethyl-3-(3-methylaminopropyl)-carbodiimide (EDC) and N-hydroxysuccinimide (NHS) an enzyme becomes covalently bound via a primary amino groups.

GLOD contains less amino groups than GPT and enzymes have different iso-electric points. For an optimal coupling GLOD was reacted 25 minutes in formate buffer (pH=3), followed by 10 minutes coupling of GPT in maleate buffer (pH=6).

After the covalent binding of the enzyme on the activated surface, the remaining NHS esters were deactivated by washing with ethanolamine or PEG-amine.

Example 2

Preparation of a Surface Layer

A bienzyme pair of Glutamate Oxidase (GLOD) and Glutamate Pyruvate Transaminase (GPT) is immobilised on a tantalum pentoxide ($Ta_2O_5$) surface of the proton sensitive gate layer of an ion sensitive field-effect transistor.
A silane triethoxysilylundecanal (TESU) self-assembled monolayer is deposited on the oxide surface. The functional group of this silane layer for immobilising the enzymes is an aldehyde, which can directly couple to the amino groups of the enzymes. After coupling cyanoborohydride is used to reduce the bond between the amino group and the aldehyde group and as such to stabilise it.

In order to improve the binding of the enzymes to this aldehyde monolayer, poly-L-lysine (PLL) is deposited after silanisation as an intermediate layer, whereafter the enzymes are coupled to PLL with glutaraldehyde.

Example 3

Microcontact Printing

Microcontact printing is performed using an elastomeric stamp comprised of a mixture of poly(dimethylsulfoxide) (PDMS) and a hardener, which is poured into a mould set against a patterned master and cured at high temperature, typically 110° C. The ratio of PDMS to hardener can vary depending on the desired softness or hardness the cured stamp. Typical ratios are 10/1 PDMS/hardener. Since the cured stamps are hydrophobic, they are good candidates for depositing hydrophilic molecules and polymers onto favourable surfaces since they will not irreversibly bind to the surface of the stamp and will readily transfer to the more favourable substrate surface. However, to improve the inking of such molecules, the molecules must be able to diffuse into the stamp. Methods of improving this diffusion include immersing the cured stamp in water for one week prior to use.

The flip chip bonder is used to align and print the bienzyme system onto the surface of the sensor. The lower substrate can be the sensor. The stamp is inked with one enzyme from the bienzyme system and loaded onto the arm. It is flipped and then aligned with the features of the sensor, which can include the electrodes or other reference points. The bonding phase is the point at which the stamp comes into contact with the sensor and prints the enzyme onto the sensor surface. Pressure can be used during the bonding phase to ensure that conformal contact between the stamp and the surface is achieved. Pressure ranges are typically 0-1 kg. This process can be repeated with a second stamp of a different but complementary pattern and the second enzyme. Because of the alignment feature, the two enzymes can thus be printed in a controlled and precise manner that is limited only by the patterns on the stamp. For example, if the two stamps being used are of a complementary nature, the resulting pattern can be that the two enzymes are directly next to each other. The alignment feature also allows the user to align the enzymes in such a way as to leave the electrodes of the sensor free of enzyme and, thus, controlling where the immobilisation layer is left unprinted with enzymes. This enzyme-free region creates a cell-adhering region to which cells are able to attach.

Figure 4:
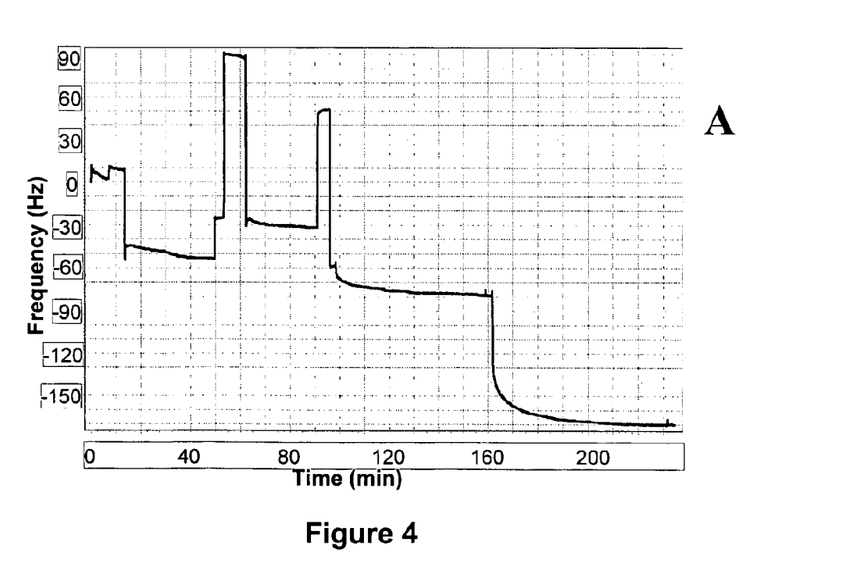
FIG. 4 shows Quartz Crystal Microbalance (QCM) graphs for the immobilisation of GLOD and GPT according to an embodiment of the invention. The ratio of the immobilisation is controllable and reproducible with the surface chemistry used in this assay. Ratio graph A=4.5; ratio graph B=4.2.
Figure 5:
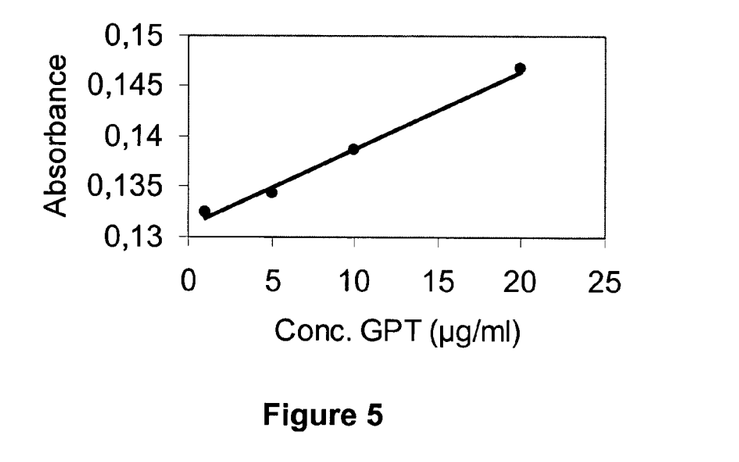
FIG. 5 shows the increase in absorbance of a colorimetric assay solution with increasing concentrations of GPT according to an embodiment of the invention. A fixed concentration of glutamate, Glutamate Oxidase and alanine was used while the concentration of Glutamate Pyruvate Transaminase was varied.
Figure 6:
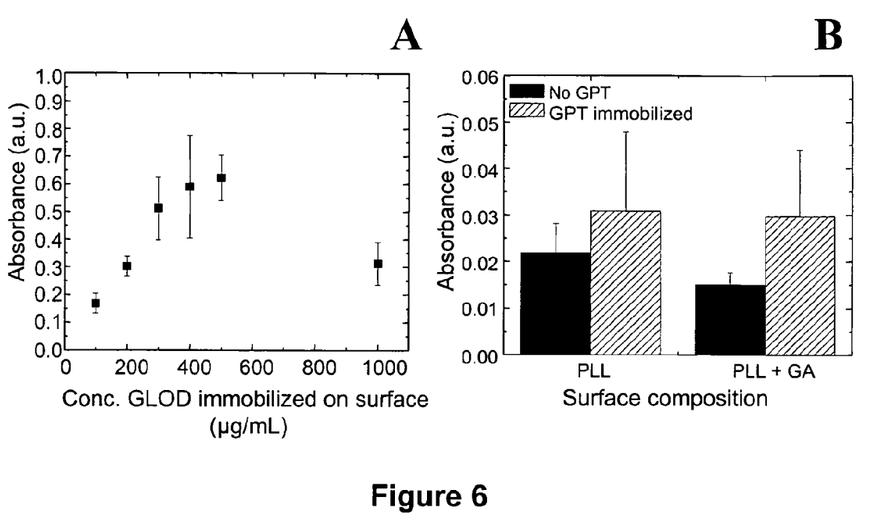
FIG. 6 shows the amplification of glutamate by a colorimetric assay according to an embodiment of the invention. Panel A: GPT in solution and immobilised Glutamate Oxidase (GLOB). Panel B: Amplification by patterned co-immobilisation of GLOD and GPT on Poly-L-lysine (PLL) and PLL and glutaraldehyde (PLL+GA) surfaces. GLOD was immobilised by microcontact printing, and GPT was immobilised overnight by cross-linking.

The enzymes of the bienzyme system are deposited in a controlled way. Both enzymes are immobilised in a specific relationship in order to get the maximal amplification. Therefore, the surface chemistry has to be reproducible and controllable. Quartz Crystal Microbalance (QCM) measurements were made on this surface chemistry and the results are shown in FIG. 4. A quartz crystal microbalance can detect the addition or removal of mass by measuring the change in frequency of a quartz crystal resonator. As mass is deposited or removed from the surface of the crystal, the thickness changes and, thus, the frequency of oscillation will also change. This frequency change can be correlated to the mass change. The QCM crystals that were used had 100 nm $Ta_2O_5$ deposited on the surface. After silanization with triethoxysilylundecanal (TESU), the crystals were loaded into the QCM apparatus, where poly-L-lysine (PLL) was then coupled to the TESU surface, followed by glutaraldehyde, GLOD, and finally GPT coupling. The results shown in FIG. 4 demonstrate that with a fixed concentration of both GLOD and GPT, the same ratio can be obtained on the surface chemistry layer, thus leading to controlled and reproducible enzyme deposition.

Example 4

Application of Cells

A poly-L-lysine (PLL) layer serves as the first region for cell attachment. It is deposited on top of the triethoxysilylundecanal (TESU) surface layer in a 2 mg/mL solution in borate buffer for 30 minutes. The amino groups of the PLL react with the aldehyde groups of the TESU layer, thus producing an imide bond. This reactive imide bond is then reduced to a more stable single bond through a second reaction with cyanoborohydride. The positively-charged PLL surface promotes the attachment of cells, thus creating a cell-adhering region.

The cells deposited on the surface layer are neuronal cells. Hippocampal neurons are isolated from E18 FVB strain mice. Timed-pregnant rats are euthanised and embryos removed. Hippocampi are dissected from both hemispheres in sterile Hepes buffered saline solution and incubated in 0.25% trypsin for 15 minutes in an incubator at 37° C. and 5% $CO_2$ atmosphere. After trypsinization, cells are washed three times with HBSS and mechanically dissociated by the use of fire polished Pasteur pipettes. The number of cells originating from half a hippocampus are seeded per 6 cm dish containing one substrate. Cells are seeded in Neurobasal medium containing 2% B27 supplement and 0.125% glutamate. After 4 hours, the substrates are placed into dishes with a confluent monolayer of glia cells, such that the neurons are facing the glia feeding layer. The substrates are suspended upside down above the feeding layer. After 4 days in co-culture, the media is changed from Neurobasal medium containing glutamate to Neurobasal medium without glutamate. The glia cells are cultured one week before the hippocampal culture from newborn FVB pups in the same manner as described for the hippocampal culture, except that these are seeded in 6 cm dishes coated with PLL and containing MEM medium supplemented with 10% Horse serum.

Example 5

Detection of Glutamate Production by Neuronal Cells

The surface layer of the sensor includes a poly-L-lysine (PLL) layer with the bienzymatic system of Glutamate Oxidase (GLOD) and Glutamate Pyruvate Transaminase (GPT). The two enzymes are aligned on the surface layer in a defined pattern. Furthermore, the two enzymes are aligned such that adequate cell-adhering regions of PLL are still accessible to the neuronal cells. As a result, The cells on the PLL regions occur in defined pattern. The PLL regions serve as a cell-adhering region, allowing for the attachment and directed growth of the neurons. In this device GLOD is in close proximity to the neurons and converts secreted glutamate, with generation of ammonia and hydrogen peroxide, creating a local pH change. This local pH change is detected by the sensor. In the presence of GPT, the glutamate is regenerated and reacts again with GLOD to produce an enhanced local pH change. In this way, the detectable moiety is amplified and the signal is heightened.

The invention claimed is:

1. A biosensor, the biosensor comprising:
a sensor configured to detect a change in a charge distribution;
a sensing layer, wherein the sensing layer is situated on the sensor; and
a surface layer, wherein the surface layer is situated on the sensing layer, and wherein the surface layer comprises a first region that is enzyme-free and adapted for adherent growth of cells and a second region, adjacent to the first region, wherein the second region is configured for attachment of proteins and comprises a bienzyme system, wherein the bienzyme system is adapted for conversion of a compound produced by the cells into a product which generates a signal detectable by the sensor, wherein the first region and the second region are separated from each other but in contact with the sensing layer, wherein at least one of the first region and the second region comprises a pattern of a plurality of linear elements, and wherein the first region and the second region are configured such that the cells row exclusively in the first region.

2. The biosensor of claim 1, further comprising cells on the first region.

3. The biosensor of claim 1, wherein at least one of the first region and the second region comprises a grid like pattern of a plurality of linear elements.

4. The biosensor of claim 3, wherein the linear elements of the first region have a width of from about 5 micrometers to about 20 micrometers.

5. The biosensor of claim 3, wherein the linear elements of the second region have a width of from about 2 micrometers to about 20 micrometers and a thickness of less than 0.5 micrometers.

6. The biosensor of claim 1, wherein the cells are neuronal cells.

7. The biosensor of claim 1, wherein the bienzyme system comprises L-glutamate pyruvate transaminase in combination with glutamate oxidase or glutamate dehydrogenase.

8. The biosensor of claim 1 wherein the compound produced by the cells is a neurotransmitter.

9. The biosensor of claim 8, wherein the neurotransmitter is glutamate.

10. A method for detection of production of a compound by cells, the method comprising:
providing a biosensor comprising: a sensor configured to detect a change in a charge distribution; a sensing layer, wherein the sensing layer is situated on the sensor; and a surface layer, wherein the surface layer is situated on the sensing layer, and wherein the surface layer comprises a first region that is enzyme-free and adapted for adherent growth of cells and a second region, adjacent to the first region, wherein the second region is configured for attachment of proteins and comprises a bienzyme system, wherein the bienzyme system is adapted for conversion of a compound produced by the cells into a product which generates a signal detectable by the sensor, wherein the first region and the second region are separated from each other but in contact with the sensing layer, and wherein at least one of the first region and the second region comprises a pattern of a plurality of linear elements, and wherein the first region and the second region are configured such that the cells grow exclusively in the first region;
providing cells, wherein the cells undergo adherent growth on the first region of the sensor, whereby the compound is produced;
converting, by the bienzyme system of the second region, the compound into the product which generates a change in a charge distribution in the sensing layer; and
detecting the change in the charge distribution by the sensor of the biosensor, whereby production of the compound by the cells is detected.

11. The method of claim 10, wherein the detectable signal is a change in pH.

12. The method of claim 10, wherein the cells are neuronal cells and the compound is a neurotransmitter.

13. The biosensor of claim 1, wherein the sensor is selected from the group consisting of a field effect transistor, a capacitive sensor, and a microelectrode.

14. The biosensor of claim 13, wherein the sensor is a field effect transistor.

15. The biosensor of claim 14, wherein the field effect transistor is an ion-selective field-effect transistor.

16. The biosensor of claim 14, wherein the biosensor is configured such that the signal modifies a conductivity in a channel region of the field effect transistor.

17. The biosensor of claim 7, wherein the second region comprises a pattern of longitudinal lines of glutamate oxidase or glutamate dehydrogenase and a pattern of traverse lines of L-glutamate-pyruvate-transaminase.

18. The biosensor of claim 13, further comprising a reference electrode, wherein the sensor is a microelectrode comprising a pH sensitive layer, and wherein the biosensor is configured to measure a change voltage difference across the pH sensitive layer that arises from a change in pH or from a different charging of a double layer capacitance.

19. The method of claim 10, wherein the sensor is a field effect transistor, and wherein a channel region of the field effect transistor is underneath the sensing layer.

20. The method of claim 19, wherein the detectable signal modifies a conductivity in the channel region of the field effect transistor.

21. The biosensor of claim 15, wherein the sensing layer is a pH sensitive gate layer, and wherein the biosensor is configured such that a change in charge distribution adsorbed at or created near the pH sensitive gate layer modulate a conductivity of a channel underneath.

22. The biosensor of claim 1, wherein the bienzyme system is spotted at dedicated places, such that, in use, the product is locally concentrated.

23. The biosensor of claim 1, wherein enzymes of the bienzyme system are immobilized in a ratio of from 100/1 to 1/100.

24. The biosensor of claim 1, wherein enzymes of the bienzyme system are immobilized in a ratio of from 5/1 to 1/5.

25. The biosensor of claim 1, further comprising a physical barrier configured to avoid growth of the cells outside of the first region.

26. The biosensor of claim 1, further comprising a chemical barrier configured to avoid growth of the cells outside of the first region.

* * * * *

UNITED STATES PATENT AND TRADEMARK OFFICE
CERTIFICATE OF CORRECTION

| | | |
|---|---|---|
| PATENT NO. | : 8,569,006 B2 | Page 1 of 1 |
| APPLICATION NO. | : 12/919725 | |
| DATED | : October 29, 2013 | |
| INVENTOR(S) | : Braeken et al. | |

It is certified that error appears in the above-identified patent and that said Letters Patent is hereby corrected as shown below:

In the Specification

In column 3 at line 13, Change "to comprising" to --comprising--.

In column 5 at line 15, Change "(GLOB)." to --(GLOD).--.

In the Claims

In column 15 at line 22, In Claim 1, change "row" to --grow--.

In column 16 at line 33, In Claim 18, change "change" to --change in--.

Signed and Sealed this
Seventeenth Day of June, 2014

Michelle K. Lee
*Deputy Director of the United States Patent and Trademark Office*